United States Patent
Zhang et al.

(10) Patent No.: US 10,314,806 B2
(45) Date of Patent: *Jun. 11, 2019

(54) PREPARATION CONTAINING CHLOROGENIC ACID CRYSTAL FORM AND USE THEREOF

(71) Applicant: SICHUAN JIUZHANG BIOLOGICAL SCIENCE AND TECHNOLOGY CO., LTD., Chengdu, Sichuan (CN)

(72) Inventors: Jie Zhang, Sichuan (CN); Lina Zhu, Sichuan (CN); Wang Huang, Sichuan (CN); Liang Zhang, Sichuan (CN)

(73) Assignee: SICHUAN JIUZHANG BIOLOGICAL SCIENCE AND TECHNOLOGY CO., LTD., Chengdu, Sichuan (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/528,996

(22) PCT Filed: Nov. 18, 2015

(86) PCT No.: PCT/CN2015/094869
§ 371 (c)(1),
(2) Date: May 23, 2017

(87) PCT Pub. No.: WO2016/082703
PCT Pub. Date: Jun. 2, 2016

(65) Prior Publication Data
US 2017/0319530 A1  Nov. 9, 2017

(30) Foreign Application Priority Data
Nov. 24, 2014  (CN) .......................... 2014 1 0680646

(51) Int. Cl.
| | | |
|---|---|---|
| A61K 31/235 | (2006.01) | |
| C07C 69/76 | (2006.01) | |
| A61K 31/216 | (2006.01) | |
| A61K 9/19 | (2006.01) | |
| A61K 9/00 | (2006.01) | |
| A61K 45/06 | (2006.01) | |
| A61K 47/02 | (2006.01) | |
| A61K 47/26 | (2006.01) | |

(52) U.S. Cl.
CPC .......... *A61K 31/216* (2013.01); *A61K 9/0019* (2013.01); *A61K 9/0053* (2013.01); *A61K 9/19* (2013.01); *A61K 45/06* (2013.01); *A61K 47/02* (2013.01); *A61K 47/26* (2013.01)

(58) Field of Classification Search
None
See application file for complete search history.

(56) References Cited

FOREIGN PATENT DOCUMENTS

| CN | 102746153 A | 10/2012 |
|---|---|---|
| CN | 102755366 A | 10/2012 |
| CN | 102786417 A | 11/2012 |
| CN | 102476997 | * 4/2014 |
| CN | 103951562 A | 7/2014 |

* cited by examiner

*Primary Examiner* — Shobha Kantamneni
(74) *Attorney, Agent, or Firm* — Novick, Kim & Lee, PLLC; Allen Xue (57) ABSTRACT

A preparation containing a chlorogenic acid crystal form. The crystal form is an orthorhombic crystal system, a space group is $P2_12_12_1$, cell parameters are as follows: a=7.7291(2)Å, b=10.9808(2)Å, c=36.5334(7)Å, α=β=γ=90.00°, Z=8, and a cell volume is 3100.65(11)Å3. The content of the chlorogenic acid crystal form in the preparation is 10-5000 mg/g. The preparation is advantageous to bioavailability, and can be used for preparing medicines for treating tumor, psoriasis and other immune system diseases, resisting oxidation, protecting liver and gallbladder, treating cardiovascular diseases, and resisting viruses.

15 Claims, 2 Drawing Sheets

PREPARATION CONTAINING CHLOROGENIC ACID CRYSTAL FORM AND USE THEREOF

TECHNICAL FIELD

The present invention relates to a preparation containing chlorogenic acid crystal form and uses thereof, and belongs to pharmaceutical preparation field.

BACKGROUND ART

Chlorogenic acid is a phenolic acid condensated by caffeic acid and quinic acid, and belongs to phenylpropanoid compounds produced by shikimic acid pathway in plant during aerobic respiration process.

Chlorogenic acid has a wide biological activity, and study of modern science on bioactivities of chlorogenic acid has already covered many fields such as food, health care, medicine, household chemicals and so on. Chlorogenic acid is an important bioactive agent, and possesses many actions such as antibacterial, anti-virus, increasing leukocytes, liver protection and cholaneresis, anti-tumor, lowering blood pressure, reducing blood fat, scavenging free radicals, and exciting central nervous system.

However, the chlorogenic acid preparation in prior art mostly exists in amorphous forms, and thus the applicable effect has significant deviation.

Available references report chlorogenic acid has diverse crystal forms, but there is no report studying on therapeutic effect comparison of crystal form preparations of chlorogenic acid. Because different crystal forms present in the same pharmaceutical preparations usually produce obvious differences in appearance, dissolubility, melting point, density, and similar physico-chemical properties, as well as differences in drug dissolution, biological availability, etc., different crystal forms can affect therapeutic playing such as drug stability, bioavailability, etc.

Effect of crystal forms on pharmacodynamics of drugs is a more interesting issue in current pharmaceutical research, and for the difference in therapeutic effect of a same drug, except for the reasons of different quality caused by different production technology, another possible factor is the impact of drug crystal form. Because of different dissolubility and dissolution rate, different crystal forms of drug thus influence bioavailability, and then lead to difference in clinical efficacy. References report that cimetidine has many crystal forms including types A, B, C, and so on, and only A type is the most potent, but domestic cimetidine is generally not absolute A type, thus affects curative effect. Antiulcer drug famotidine has four crystal forms, and their melting point, IR spectra and physicochemical properties show obvious differences, and for inhibitory activity of gastric acid secretion, B type is more potent than A type. For some drugs, therapeutic effects of crystalline states are not better than non-crystal forms, such as suspension of amorphous novobiocin.

CONTENT OF THE INVENTION

Based on above technical problems, the object of the present invention is intended to provide a preparation containing specific chlorogenic acid and its dosage.

Above object of the present invention is realized by following technical solutions:

A preparation contain chlorogenic acid crystal forms, in which the crystal form is an orthorhombic system, the space group is $P2_12_12_1$, cell parameters are as follows: a=7.7291(2)Å, b=10.9808(2)Å, c=36.5334(7)Å, α=β=γ=90.00°, Z=8, and the cell volume is 3100.65(11)Å3; the clinical dosage of said preparation is 1.0-20 mg/kg per day.

In the present invention, the content of chlorogenic acid crystal forms is preferably 10-500 mg/g, dependent on different dosage forms.

In the present invention, the dosage forms of said preparations may be those conventional, including but not limited to oral preparations, injections, respiratory tract delivery preparations, skin delivery preparations, mucosal delivery preparation, etc.

By researching, the applicants discover that controlling crystal forms of chlorogenic acid in preparations can obviously improve therapeutic effects. Further, the applicants discover that when the content of chlorogenic acid is 10-60 mg/kg, the preparations have obviously inhibitory actions on mice-transplanted tumors of human glioma, hepatocellular carcinoma, lung cancer, breast cancer, and so on, and have better effects, preferably using 20-40 mg/kg. According to the dosage conversion relationship of animal and human, the clinical dosage of lyophilized powder injections of chlorogenic acid is 1.0-6.0 mg/kg per day, preferably 2-4 mg/kg per day.

Further, the applicants find that when the content of chlorogenic acid in oral preparation is 20-200 mg/kg, the preparation shows obviously protective actions on liver, and has better effects, preferably using 50-140 mg/kg. According to the dosage conversion relationship of animal and human, the clinical dosage of chlorogenic acid in oral preparation is 2 mg-20 mg/kg per day, preferably 5-14 mg/kg per day.

In the present invention, the oral preparations and injections are prepared from chlorogenic acid or chlorogenic acid and pharmaceutically acceptable excipients.

In the present invention, the crystal form of chlorogenic acid can be prepared by the way recorded in Chinese patent application CN201410193699.8, and the lyophilized powder injections can also be practiced by the way recorded in Chinese patent application CN201310366945.0.

Further, in the present invention, the lyophilized powder injections include following constituents:

Chlorogenic acid crystal 10-40 weight parts
Antioxidants 1-5 weight parts
Scaffolds 60-100 weight parts Preferably, the chlorogenic acid crystals in lyophilized powder injections are 30-40 weight parts; antioxidants are preferably 2-5 weight parts; scaffolds are preferably 80-90 weight parts. The antioxidant is sodium bisulfite, and the scaffold is mannitol.

In a specific example of the present invention, the lyophilized powder injections include following constituents per 1000 preparation units:

| | |
|---|---|
| Chlorogenic acid crystal | 30 g |
| Antioxidants | 2 g |
| Scaffolds | 80 g |

Injectable water was added to 2000 ml.

Further, the oral preparation of the present invention includes following constituents:

Chlorogenic acid crystal 80-150 weight parts
Bulking agents 700-900 weight parts
Adhesive agents 20-220 weight parts.

Preferably, the chlorogenic acid crystal is preferably 80-100 weight parts; the bulking agent is preferably 800-900 weight parts; the adhesive agent is preferably 100-220 weight parts.

In above oral preparations, the bulking agents include but are not limited to one kind or several kinds selected from starch, sugar, dextrin, lactose, amylum pregelatinisatum, microcrystalline cellulose, calcium sulfate, calcium hydrogen phosphate or mannitol; the adhesive agents include but are not limited to one kind or several kinds selected from carboxymethylcellulose sodium, hydroxypropyl cellulose, methyl cellulose, ethyl cellulose, polyvinylpyrrolidone.

In a specific example of the present invention, the oral preparations include following constituents per 1000 preparation units:

| | |
|---|---|
| Chlorogenic acid crystal | 100 g |
| Bulking agents | 800 g |
| Adhesive agents | 100 g |

Another object of the present invention is intended to provide applications of one kind of above preparations in preparation of drugs for treatment of tumors, psoriasis and similar immune system disorders, cardiovascular diseases, together with preparation of antioxidant drugs, hepatoprotective and cholagogic drugs, and anti-virus drugs, etc., in particular, including but not limited to small cell lung cancer, liver cancer, breast cancer, brain tumor, psoriasis.

Beneficial effects of the present invention include: the crystal form preparation of chlorogenic acid according to the present invention is better for playing curative effectiveness of drugs such as bioavailability and the like, and the crystal is the dominant crystal form for playing therapeutic effects of chlorogenic acid, and exerts better therapeutic effects on uses in drugs for treatment of tumors, psoriasis and similar immune system disorders, cardiovascular diseases, together with uses in antioxidant drugs, hepatoprotective and cholagogic drugs, and anti-virus drugs, etc. Moreover, the present invention provides the effective dose of crystal form preparation of chlorogenic acid used in clinical, and provides evidences for safety and effectiveness of crystal form preparation of chlorogenic acid in clinical.

EXAMPLES

Example 1

Preparation of Lyophilized Powder Injections

The formulation was determined as 1000 preparation units (30 mg/injection):

| | |
|---|---|
| Chlorogenic acid crystal | 30 g |
| Antioxidants | 2 g |
| Scaffolds | 80 g |

Injectable water was added to 2000 ml;

According to above formulation, the raw materials were weighed, and injectable water was taken out, to which antioxidants (such as sodium bisulfite), chlorogenic acid crystal, scaffolds (such as mannitol) were successively added and thoroughly dissolved under stirring, and pH values were regulated in the range of 2-4; the temperature of injectable water was 45-50° C., with addition of 0.03% active carbon, and after stirring for 30 min, the mixture was filtered to remove the active carbon, then filtered with 0.22 μm hydrophilic micro pore film until the filtrate is clear, followed by aseptic canning and freeze-drying, to obtain lyophilized powder injections.

Example 2

Preparation of Oral Preparations

The formulation was determined as 1000 preparation units (100 mg/tablet):

| | |
|---|---|
| Chlorogenic acid crystal | 100 g |
| Bulking agents | 800 g |
| Adhesive agents | 100 g |

Suitable amount of bulking agents and adhesive agents were added to chlorogenic acid crystal, Adhesive agents were added to suitable amount of chlorogenic acid crystal forms, then adhesive agent was added, and followed by sieving, mixing, granulating, processing granules, addition of suitable amount of lubricants, and tableting.

Example 3

Uses for Treatment of Lung Cancer

Animal C57BL/6 mice, body weight 13~20 g, half male and half female.

Cell Lines Lewis cells were mice lung cancer cells, and grew adhering to the wall in RPMI-1640 media containing 10% calf serum, 100 U·ml$^{-1}$ penicillin, 100 μg·ml$^{-1}$ streptomycin, and were cultured in an incubator at 37° C. under 5% $CO_2$, followed by changing the medium and subculturing every two or three days.

Cell Culture Cells were routinely recovered and subcultured, and then after Lewis cells in logarithmic phase of growth were digested with 0.25% trypsin and left the wall, RPMI-1640 culture solution was added, and cells were gently blown to make a suspension, followed by centrifugating at 1000 rpm for 5 min and washing twice. Viable cells were counted by trypan blue staining. Cell suspension was subcutaneously inoculated at the left forelimb armpit of mice at 0.2 ml/animal (containing about $1\times10^7$ cells), and after tumor grew to 1 cm×1 cm×1 cm, mice were used in experiment. Mice tumors were aseptically stripped, and washed with Hank's solution thrice, to remove blood, fat and necrotic tissues. Tumors were cut to broken pieces of 1 mm×1 mm×1 mm, and washed with Hank's solution twice, to which physiological saline was added at a ratio of (1 g:3 ml), and then ground in a glass homogenizer and filtered by 80-100 mesh sieve to make a suspension of single cell. Viable cells were counted by trypan blue staining.

(4) Administration Experiment

Prepared cell suspension was inoculated at the left forelimb armpit of mice at 0.2 ml/animal (containing about $1\times10^7$ cells), and mice were randomly divided into groups, 10 mice for each group, including chlorogenic acid groups respectively administered with a dosage of 100 mg·kg$^{-1}$, 90 mg·kg$^{-1}$, 80 mg·kg$^{-1}$, 70 mg·kg$^{-1}$, 60 mg·kg$^{-1}$, 50 mg·kg$^{-1}$, 40 mg·kg$^{-1}$, 30 mg·kg$^{-1}$, 20 mg·kg$^{-1}$, 10 mg·kg$^{-1}$, 5 mg·kg$^{-1}$, 1 mg·kg$^{-1}$, and a negative control group (N.S, normal saline). On the second day after inoculation, a dosage of 0.2 ml·10 g$^{-1}$ was administrated to each group by peritoneal injection (ip) for successive 12 times, once a day. When the tumor weight in negative control group was more than 1.0 g (tumor volume being about 0.5 cm$^3$), the experiment was stopped, and mice were sacrificed by cervical vertebrae removal and weighed. Tumors were stripped to calculate inhibitory rate.

Inhibitory rate %=[1−(The mean tumor weight of drug groups/The mean tumor weight of control group)]×100%

(5) Experimental Results

Figure 1:
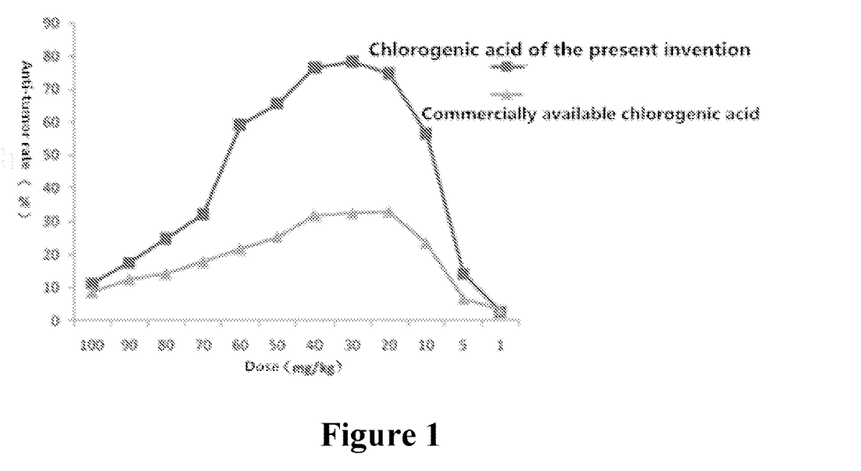
FIG. 1 is the effect contrast diagram of chlorogenic acid according to the present invention and commercially available chlorogenic acid for inhibitory rate of mice-transplanted tumor of Lewis lung cancer C57BL/6.

As shown in Table 1 and FIG. 1, chlorogenic acid of the present invention has an obviously inhibitory action on mice-transplanted tumor of Lewis lung cancer C57BL/6, and compared with the negative control group, the inhibition has a statistical difference. And in the dosage groups of 10 mg/kg-60 mg/kg, the inhibitory action is obvious.

Cell Lines H22 cell lines were mice liver cancer cells, and were subjected to suspension growth in RPMI-1640 media containing 10% calf serum, 100 U·ml$^{-1}$ penicillin, 100 μg·ml$^{-1}$ streptomycin, and cultured in an incubator at 37° C. under 5% $CO_2$, followed by changing the medium and subculturing every two or three days.

Cell Culture H22 cells in exponential phase of growth were collected, centrifugated at 1000 rpm for 5 min, and washed twice. Viable cells were counted by trypan blue staining. The cells were quickly inoculated in abdominal cavity of KM mice, and after 7~10 days, ascites were drawn and subcutaneously inoculated at the left forelimb armpit of mice at 0.2 ml/animal (containing about $2\times10^7$ cells). When tumor grew to 1 cm×1 cm×1 cm, mice were used in experiment. Mice tumors were aseptically stripped, and washed with Hank's solution thrice, to remove blood, fat and necrotic tissues. Tumors were cut to broken pieces of 1 mm×1 mm×1 mm, and washed with Hank's solution twice, to which physiological saline was added at a ratio of (1 g:3 ml), and then ground in a glass homogenizer and filtered by 80-100 mesh sieve to make a suspension of single cell. Viable cells were counted by trypan blue staining.

(4) Administration Experiment

Prepared cell suspension was inoculated at the left forelimb armpit of KM mice at 0.2 ml/animal (containing about $1\times10^6$ cells), and mice were randomly divided into groups, 10 mice for each group, including chlorogenic acid groups respectively administered with a dosage of 100 mg·kg$^{-1}$, 90 mg·kg$^{-1}$, 80 mg·kg$^{-1}$, 70 mg·kg$^{-1}$, 60 mg·kg$^{-1}$, 50 mg·kg$^{-1}$,

TABLE 1

Effects of chlorogenic acid according to the present invention on the weight and the inhibition of mice-transplanted tumor of Lewis lung cancer ($\bar{x} \pm s$)

| Groups | Dose (mg · kg$^{-1}$) | Animal number (n) | Tumor weight (g) | Inhibitory rate (%) |
|---|---|---|---|---|
| Chlorogenic acid of the present invention | 100 | 10 | 1.316 ± 0.352 | 11.3 |
| Chlorogenic acid of the present invention | 90 | 10 | 1.223 ± 0.314 | 17.6 |
| Chlorogenic acid of the present invention | 80 | 10 | 1.116 ± 0.513 | 24.8 |
| Chlorogenic acid of the present invention | 70 | 10 | 1.005 ± 0.657 | 32.3 |
| Chlorogenic acid of the present invention | 60 | 10 | 0.605 ± 0.363* | 59.2 |
| Chlorogenic acid of the present invention | 50 | 10 | 0.510 ± 0.241* | 65.6 |
| Chlorogenic acid of the present invention | 40 | 10 | 0.350 ± 0.078** | 76.4 |
| Chlorogenic acid of the present invention | 30 | 10 | 0.322 ± 0.111** | 78.3 |
| Chlorogenic acid of the present invention | 20 | 10 | 0.377 ± 0.083** | 74.6 |
| Chlorogenic acid of the present invention | 10 | 10 | 0.646 ± 0.230* | 56.5 |
| Chlorogenic acid of the present invention | 5 | 10 | 1.273 ± 0.258 | 14.2 |
| Chlorogenic acid of the present invention | 1 | 10 | 1.445 ± 0.772 | 2.6 |
| Commercially available chlorogenic acid | 100 | 10 | 1.356 ± 0.338 | 8.6 |
| Commercially available chlorogenic acid | 90 | 10 | 1.300 ± 0.462 | 12.4 |
| Commercially available chlorogenic acid | 80 | 10 | 1.273 ± 0.511 | 14.2 |
| Commercially available chlorogenic acid | 70 | 10 | 1.220 ± 0.237 | 17.8 |
| Commercially available chlorogenic acid | 60 | 10 | 1.163 ± 0.443 | 21.6 |
| Commercially available chlorogenic acid | 50 | 10 | 1.109 ± 0.254 | 25.3 |
| Commercially available chlorogenic acid | 40 | 10 | 1.012 ± 0.369 | 31.8 |
| Commercially available chlorogenic acid | 30 | 10 | 1.001 ± 0.204 | 32.5 |
| Commercially available chlorogenic acid | 20 | 10 | 0.996 ± 0.428 | 32.9 |
| Commercially available chlorogenic acid | 10 | 10 | 1.135 ± 0.556 | 23.5 |
| Commercially available chlorogenic acid | 5 | 10 | 1.386 ± 0.398 | 6.6 |
| Commercially available chlorogenic acid | 1 | 10 | 1.437 ± 0.466 | 3.2 |
| Negative group | N.S | 10 | 1.484 ± 0.392 | — |

Compared with the negative group, *p < 0.05, **p < 0.01.

Example 4

Uses for Treatment of Liver Cancer (1) Animal Kunming mice, half male and half female, body weight 16~27 g.

40 mg·kg$^{-1}$, 30 mg·kg$^{-1}$, 20 mg·kg$^{-1}$, 10 mg·kg$^{-1}$, 5 mg·kg$^{-1}$, 1 mg·kg$^{-1}$, and a negative control group (N.S, normal saline). On the second day after inoculation, a dosage of 0.2 ml·10 g$^{-1}$ was administrated by intravenous injection (iv), once a day. When the average tumor weight in negative group was more than 1.0 g (tumor volume being about 0.5 cm$^3$), the experiment was stopped, and mice were sacrificed by cervical vertebrae removal and weighed. Tumors were stripped to calculate inhibitory rate.

(5) Experimental Results

Figure 2:
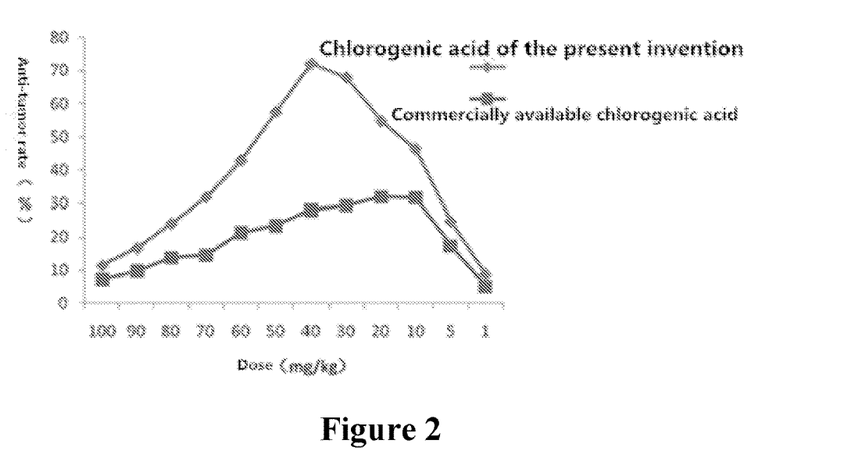
FIG. 2 is the effect contrast diagram of chlorogenic acid according to the present invention and commercially available chlorogenic acid for inhibitory rate of mice-transplanted tumor of H22 liver cancer KM.

As shown in Table 2 and FIG. 2, chlorogenic acid of the present invention has an obviously inhibitory action on KM mice-transplanted tumor of H22 liver cancer, and compared with the negative control group, the inhibition has a statistical difference. And in the dosage groups of 10 mg/kg-60 mg/kg, the inhibitory action is obvious.

experiment. Mice tumors were aseptically stripped, and washed with Hank's solution thrice, to remove blood, fat and necrotic tissues. Tumors were cut to broken pieces of 1 mm×1 mm×1 mm, and washed with Hank's solution twice, to which physiological saline was added at a ratio of (1 g:3 ml), and then ground in a glass homogenizer and filtered by 80-100 mesh sieve to make a suspension of single cell. Viable cells were counted by trypan blue staining.

TABLE 2

Effects of chlorogenic acid according to the present invention on the weight and the inhibition of M mice-transplanted tumor of H22 liver cancer ($\bar{x} \pm s$)

| Groups | Dose (mg · kg$^{-1}$) | Animal number (n) | Tumor weight (g) | Inhibitory rate (%) |
|---|---|---|---|---|
| Chlorogenic acid of the present invention | 100 | 10 | 2.078 ± 0.326 | 11.5 |
| Chlorogenic acid of the present invention | 90 | 10 | 1.956 ± 0.581 | 16.7 |
| Chlorogenic acid of the present invention | 80 | 10 | 1.782 ± 0.122 | 24.1 |
| Chlorogenic acid of the present invention | 70 | 10 | 1.599 ± 0.427 | 31.9 |
| Chlorogenic acid of the present invention | 60 | 10 | 1.341 ± 0.356* | 42.9 |
| Chlorogenic acid of the present invention | 50 | 10 | 0.998 ± 0.207** | 57.5 |
| Chlorogenic acid of the present invention | 40 | 10 | 0.653 ± 0.238** | 72.2 |
| Chlorogenic acid of the present invention | 30 | 10 | 0.754 ± 0.071** | 67.9 |
| Chlorogenic acid of the present invention | 20 | 10 | 1.061 ± 0.096** | 54.8 |
| Chlorogenic acid of the present invention | 10 | 10 | 1.261 ± 0.388* | 46.3 |
| Chlorogenic acid of the present invention | 5 | 10 | 1.768 ± 0.667 | 24.7 |
| Chlorogenic acid of the present invention | 1 | 10 | 2.141 ± 0.333 | 8.8 |
| Commercially available chlorogenic acid | 100 | 10 | 2.179 ± 0.341 | 7.2 |
| Commercially available chlorogenic acid | 90 | 10 | 2.118 ± 0.557 | 9.8 |
| Commercially available chlorogenic acid | 80 | 10 | 2.026 ± 0.611 | 13.7 |
| Commercially available chlorogenic acid | 70 | 10 | 2.005 ± 0.345 | 14.6 |
| Commercially available chlorogenic acid | 60 | 10 | 1.848 ± 0.741 | 21.3 |
| Commercially available chlorogenic acid | 50 | 10 | 1.799 ± 0.462 | 23.4 |
| Commercially available chlorogenic acid | 40 | 10 | 1.689 ± 0.149 | 28.1 |
| Commercially available chlorogenic acid | 30 | 10 | 1.598 ± 0.101 | 31.9 |
| Commercially availaavailable chlorogenic | 20 | 10 | 1.602 ± 0.283 | 31.8 |
| Commercially availaavailable chlorogenic | 10 | 10 | 1.583 ± 0.667 | 32.6 |
| Commercially available chlorogenic acid | 5 | 10 | 1.939 ± 0.357 | 17.4 |
| Commercially available chlorogenic acid | 1 | 10 | 2.228 ± 0.538 | 5.1 |
| Negative group | N.S | 10 | 2.348 ± 0.612 | — |

Compared with the negative group, *p < 0.05, **p < 0.01.

Example 5

In vivo Investigation of Inhibitory Action on BABLc Mice Transplanted Tumors Experimental Materials (1) Animal BABLc mice, ♀, body weight 17~21 g Cell Lines EMT-6 cell lines were mice breast cancer cells, and grew adhering to the wall in RPMI-1640 complete media containing 10% calf serum, 1 mmol/L glutamine, 100 U·ml$^{-1}$ penicillin and 100 μg·ml$^{-1}$ streptomycin, and were cultured in an incubator at 37° C. under 5% $CO_2$, followed by changing the medium and subculturing every two or three days.

Cell Culture Cells were routinely recovered and subcultured, and then after EMT-6 cells in logarithmic phase of growth were digested with 0.25% trypsin and left the wall, RPMI-1640 culture solution was added, and cells were gently blown to make a suspension, followed by centrifugating at 1000 rpm for 5 min and washing twice. Viable cells were counted by trypan blue staining. Cell suspension was subcutaneously inoculated at the left forelimb armpit of mice at 0.2 ml/animal (containing about 1×10$^7$ cells), and after tumor grew to 1 cm×1 cm×1 cm, mice were used in Experimental Method Prepared cell suspension was inoculated at the left forelimb armpit of BABLc mice at 0.2 ml/animal (containing about 1×10$^6$ cells), and mice were randomly divided into groups, 10 mice for each group, including chlorogenic acid groups respectively administrated with a dosage of 100 mg·kg$^{-1}$, 90 mg·kg$^{-1}$, 80 mg·kg$^{-1}$, 70 mg·kg$^{-1}$, 60 mg·kg$^{-1}$, 50 mg·kg$^{-1}$, 40 mg·kg$^{-1}$, 30 mg·kg$^{-1}$, 20 mg·kg$^{-1}$, 10 mg·kg$^{-1}$, 5 mg·kg$^{-1}$, 1 mg·kg$^{-1}$, and a negative control group (N.S, normal saline). On the second day after inoculation, a dosage of 0.2 ml·10 g$^{-1}$ was administrated to each group by intraperitoneal injection (ip) for successive 9 days, once a day. When the tumor weight in negative group was more than 1.0 g(tumor volume being about 0.5 cm$^3$), the experiment was stopped, and mice were sacrificed by cervical vertebrae removal and weighed. Tumors were stripped to calculate inhibitory rate.

Inhibitory rate %=[1−(The mean tumor weight of drug groups/The mean tumor weight of control group)]×100%

Experimental Results

Figure 3:
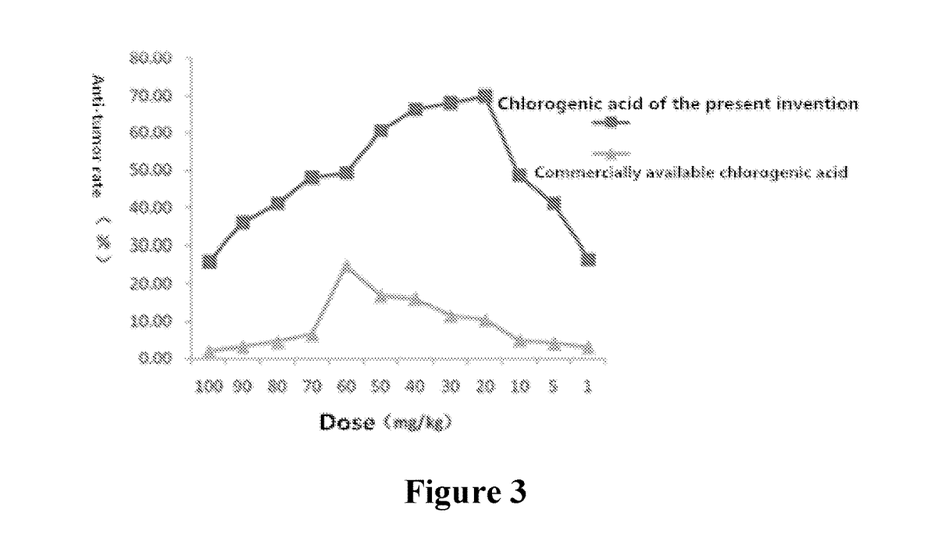
FIG. 3 is the effect contrast diagram of chlorogenic acid according to the present invention and commercially available chlorogenic acid for inhibitory rate of mice-transplanted tumor of EMT-6 breast cancer BABLc.

For effects of chlorogenic acid on the weight and the inhibition of BABLc mice-transplanted tumor of EMT-6 breast cancer, seen Table 3 and FIG. 3.

TABLE 3

Effects of chlorogenic acid on the weight and the inhibition of BABLc mice-transplanted tumor of EMT-6 breast cancer ($\overline{X} \pm s$)

| Groups | Dose (mg · kg$^{-1}$) | Animal number (n) | Tumor weight (g) | Inhibitory rate (%) |
|---|---|---|---|---|
| Chlorogenic acid of the present invention | 100 | 10 | 0.995 ± 0.0256 | 25.80 |
| Chlorogenic acid of the present invention | 90 | 10 | 0.859 ± 0.0754 | 35.94 |
| Chlorogenic acid of the present invention | 80 | 10 | 0.789 ± 0.087 | 41.16 |
| Chlorogenic acid of the present invention | 70 | 10 | 0.698 ± 0.112*** | 47.95 |
| Chlorogenic acid of the present invention | 60 | 10 | 0.681 ± 0.156*** | 49.22 |
| Chlorogenic acid of the present invention | 50 | 10 | 0.529 ± 0.168*** | 60.55 |
| Chlorogenic acid of the present invention | 40 | 10 | 0.451 ± 0.097*** | 66.37 |
| Chlorogenic acid of the present invention | 30 | 10 | 0.429 ± 0.168*** | 68.01 |
| Chlorogenic acid of the present invention | 20 | 10 | 0.403 ± 0.101*** | 69.95 |
| Chlorogenic acid of the present invention | 10 | 10 | 0.690 ± 0.188*** | 48.55 |
| Chlorogenic acid of the present invention | 5 | 10 | 0.789 ± 0.087 | 41.16 |
| Chlorogenic acid of the present invention | 1 | 10 | 0.987 ± 0.154 | 26.40 |
| Commercially available chlorogenic acid | 100 | 10 | 1.312 ± 0.087 | 2.16 |
| Commercially available chlorogenic acid | 90 | 10 | 1.298 ± 0.423 | 3.21 |
| Commercially available chlorogenic acid | 80 | 10 | 1.279 ± 0143 | 4.62 |
| Commercially available chlorogenic acid | 70 | 10 | 1.254 ± 0.514 | 6.49 |
| Commercially available chlorogenic acid | 60 | 10 | 1.009 ± 0.123 | 24.76 |
| Commercially available chlorogenic acid | 50 | 10 | 1.115 ± 0.201 | 16.85 |
| Commercially available chlorogenic acid | 40 | 10 | 1.125 ± 0.125 | 16.11 |
| Commercially available chlorogenic acid | 30 | 10 | 1.185 ± 0.247 | 11.63 |
| Commercially available chlorogenic acid | 20 | 10 | 1.201 ± 0.546 | 10.44 |
| Commercially available chlorogenic acid | 10 | 10 | 1.274 ± 0.854 | 5.00 |
| Commercially available chlorogenic acid | 5 | 10 | 1.285 ± 0.324 | 4.18 |
| Commercially available chlorogenic acid | 1 | 10 | 1.299 ± 0.253 | 3.13 |
| Negative group | N.S | 10 | 1.341 ± 0.299 | — |

Compared with the negative group, ***p < 0.001.

As shown in Table 3 and FIG. 3, chlorogenic acid of the present invention has an obviously inhibitory action on BABLc mice-transplanted tumor of EMT-6 liver cancer, and compared with the negative control group, the inhibition has a statistical difference. And in the dosage groups of 10 mg/kg-60 mg/kg, the inhibitory action is obvious.

Example 6

Investigation on Inhibitory Action of Chlorogenic Acid Against Transplanted Brain Glioma 1. Materials Human brain glioma cell lines were obtained from Key Laboratory of Transplant Engineering and Immunology, Ministry of health, West China Hospital, Sichuan University. Chlorogenic acid of the present invention is provided by SICHUAN JIUZHANG BIOLOGICAL SCIENCE AND TECHNOLOGY CO., LTD., together with chlorogenic acid commercially available.

Methods (1) Model establishment Mice were divided into groups, 10 mice for each group. The solution of brain glioblastoma cell lines was suitably diluted, and inoculated in cortex of left temporal lobe of mice, respectively.

Administration and intervention 24 h after inoculation, mice in each group were administrated by intraperitoneal injection. The mice groups were respectively the dose groups of chlorogenic acid, i.e. 100 mg·kg$^{-1}$, 90 mg·kg$^{-1}$, 80 mg·kg$^{-1}$, 70 mg·kg$^{-1}$, 60 mg·kg$^{-1}$, 50 mg·kg$^{-1}$, 40 mg·kg$^{-1}$, 30 mg·kg$^{-1}$, 20 mg·kg$^{-1}$, 10 mg·kg$^{-1}$, 5 mg·kg$^{-1}$, 1 mg·kg$^{-1}$, and the negative control group receiving the same volume of normal saline. Each group was administrated for successive 15 days.

Determination of tumor inhibitory rate On the last day, the administration was stopped, and all mice were sacrificed and dissected. Tumor tissues were stripped and weighed. Tumor inhibitory rate %=(The mean tumor weight of control group−The mean tumor weight of drug groups)[The mean tumor weight of control group]×100%.

Statistical method The variance analysis of data was performed using the statistical program software package (SPSS13.0 for Windows), and p<0.05 was considered to be a statistically significant difference.

Results

Analytic result showed that the inhibitory rate of drug groups had a trend of obvious promotion, compared with blank group, confirming chlorogenic acid had an effect on growth of tumor. The inhibitory effect of middle dose group was most significant, followed by high dose group, and specific data were given in Table 4.

TABLE 4

Effects of chlorogenic acid on the tumor weight and the inhibition of human brain glioma ($\overline{X} \pm s$)

| Groups | Dose (mg · kg$^{-1}$) | Animal number (n) | Tumor weight (g) | Inhibitmy rate (%) |
|---|---|---|---|---|
| Chlorogenic acid of the present invention | 100 | 10 | 1.331 ± 0.156 | 8.27 |
| Chlorogenic acid of the present invention | 90 | 10 | 1.259 ± 0.124 | 13.23 |
| Chlorogenic acid of the present invention | 80 | 10 | 1.189 ± 0.187 | 18.06 |
| Chlorogenic acid of the present invention | 70 | 10 | 0.998 ± 0.212 | 31.22 |
| Chlorogenic acid of the present invention | 60 | 10 | 0.701 ± 0.256*** | 51.69 |

TABLE 4-continued

Effects of chlorogenic acid on the tumor weight and the inhibition of human brain glioma ($\overline{X} \pm s$)

| Groups | Dose (mg · kg$^{-1}$) | Animal number (n) | Tumor weight (g) | Inhibitmy rate (%) |
| --- | --- | --- | --- | --- |
| Chlorogenic acid of the present invention | 50 | 10 | 0.629 ± 0.068*** | 56.65 |
| Chlorogenic acid of the present invention | 40 | 10 | 0.551 ± 0.087*** | 62.03 |
| Chlorogenic acid of the present invention | 30 | 10 | 0.456 ± 0.128*** | 68.57 |
| Chlorogenic acid of the present invention | 20 | 10 | 0.425 ± 0.151*** | 70.71 |
| Chlorogenic acid of the present invention | 10 | 10 | 0.690 ± 0.128*** | 52.45 |
| Chlorogenic acid of the present invention | 5 | 10 | 1.218 ± 0.187 | 16.06 |
| Chlorogenic acid of the present invention | 1 | 10 | 1.258 ± 0.254 | 13.30 |
| Commercially available chlorogenic acid | 100 | 10 | 1.338 ± 0.187 | 7.79 |
| Commercially available chlorogenic acid | 90 | 10 | 1.287 ± 0.323 | 11.30 |
| Commercially available chlorogenic acid | 80 | 10 | 1.275 ± 0.043 | 12.13 |
| Commercially available chlorogenic acid | 70 | 10 | 1.225 ± 0.534 | 15.58 |
| Commercially available chlorogenic acid | 60 | 10 | 1.125 ± 0.223 | 22.47 |
| Commercially available chlorogenic acid | 50 | 10 | 1.105 ± 0.301 | 23.85 |
| Commercially available chlorogenic acid | 40 | 10 | 0.988 ± 0.025 | 31.91 |
| Commercially available chlorogenic acid | 30 | 10 | 1.005 ± 0.225 | 30.74 |
| Commercially available chlorogenic acid | 20 | 10 | 1.101 ± 0.234 | 24.12 |
| Commercially available chlorogenic acid | 10 | 10 | 1.174 ± 0.154 | 19.09 |
| Commercially available chlorogenic acid | 5 | 10 | 1.289 ± 0.289 | 11.16 |
| Commercially available chlorogenic acid | 1 | 10 | 1.319 ± 0.245 | 9.10 |
| Negative group | N.S | 10 | 1.451 ± 0.225 | — |

Figure 4:
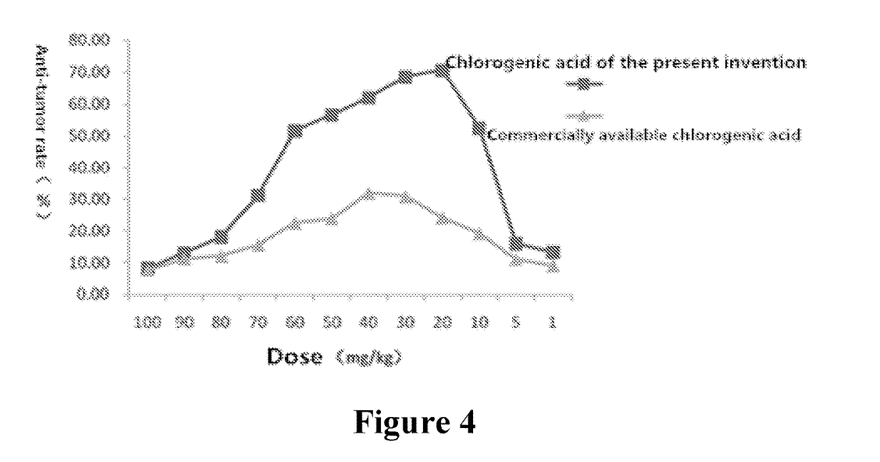
FIG. 4 is the effect contrast diagram of chlorogenic acid according to the present invention and commercially available chlorogenic acid for inhibitory rate of mice-transplanted tumor of human glioma.

As shown in Table 4 and FIG. 4, chlorogenic acid of the present invention has an obviously inhibitory action on mice-transplanted tumor of human brain glioma, and compared with the negative control group, the inhibition has a statistical difference. And in the dosage groups of 10 mg/kg-60 mg/kg, the inhibitory action is obvious.

Example 7

Protective Effect of Chlorogenic Acid on Chemical Liver Injury (Rat Alcoholic Fatty Liver Model)

1. Materials and Methods

Drug: Chlorogenic acid of the present invention is provided by SICHUAN JIUZHANG BIOLOGICAL SCIENCE AND TECHNOLOGY CO., LTD., together with chlorogenic acid commercially available.

Animal: Female SD rats, body weight 156~193 g, SPF grade.

Experimental grouping and dose design: Female SD rats were randomly divided to groups, 10 rats for each group, including dose groups of 20 mg·kg$^{-1}$, 35 mg·kg$^{-1}$, 50 mg·kg$^{-1}$, 70 mg·kg$^{-1}$, 85 mg·kg$^{-1}$, 100 mg·kg$^{-1}$, 120 mg·kg$^{-1}$, 140 mg·kg$^{-1}$, 160 mg·kg$^{-1}$, 180 mg·kg$^{-1}$, 200 mg·kg$^{-1}$, together with a negative control group and 50% ethanol model control group. Liver injury model was induced by ethanol (analytical pure).

Experimental method: Using alcoholic fatty liver model, for chlorogenic acid groups, different doses of test drug was given by intragastric administration; normal saline was given to the negative control group and the model control group, using a dosage of 10 ml/kg by one oral gavage, for successive 30 days.

2. Detection Index

Determination of ALT, AST, TG in serum of rats; Determination of SOD, MDA, reduced glutathione (GSH) in liver homogenate.

Statistics of experimental data: Statistical analysis of experimental data was performed using software package of SPSS 19.0 for windows.

Experimental Results

Effects of chlorogenic acid on the content of SOD, MDA, reduced GSH in liver homogenate of rats and the content of ALT, AST, TG in serum of rats were shown in Table 5.

As shown in Table 5, for the content of MDA, GSH, TG in rat liver homogenate of model control group, compared with the negative control group, the content of MDA and TG obviously increased (P<0.01), while the content of reduced GSH obviously decreased (P<0.01), indicating the model was successful, and the experimental system was reliable. The chlorogenic acid groups according to the present invention can all reduce the content of ALT, AST, TG, MDA in serum of rats at different degree, and improve the level of SOD and GSH; and the dosage groups of 50 mg/kg-140 mg/kg have rather obviously statistical significance.

Consequently, chlorogenic acid of the present invention had obviously inhibitory action on chemical liver injury, and the used dosage of 50 mg/kg-140 mg/kg had the most obvious effect.

TABLE 5

Effect of chlorogenic acid on the content of SOD, MDA, reduced GSH in liver homogenate of rats and the content of ALT, AST, TG in serum of rats ($\overline{X} \pm s$)

| Groups | Dose (mg · kg$^{-1}$) | Animal number (n) | SOD (nmol/mg) | MDA (U/mg) | GSH (mg/g) | TG (mg/dl) | ALT (U/L) | AST (U/L) |
| --- | --- | --- | --- | --- | --- | --- | --- | --- |
| Chlorogenic acid of the present invention | 10 | 10 | 28.12 ± 3.25 | 6.01 ± 0.45 | 13.02 ± 1.23 | 210.87 ± 4.12 | 50.12 ± 3.12 | 189.54 ± 4.87 |

TABLE 5-continued

Effect of chlorogenic acid on the content of SOD, MDA, reduced GSH in liver homogenate of rats and the content of ALT, AST, TG in serum of rats ($\overline{X} \pm s$)

| Groups | Dose (mg·kg$^{-1}$) | Animal number (n) | SOD (nmol/mg) | MDA (U/mg) | GSH (mg/g) | TG (mg/dl) | ALT (U/L) | AST (U/L) |
|---|---|---|---|---|---|---|---|---|
| Chlorogenic acid of the present invention | 20 | 10 | 36.45 ± 2.47# | 5.15 ± 0.21# | 18.98 ± 2.14# | 205.14 ± 5.65# | 48.87 ± 2.56# | 178.54 ± 6.15# |
| Chlorogenic acid of the present invention | 35 | 10 | 37.27 ± 3.25# | 5.14 ± 0.47# | 19.21 ± 1.45# | 198.56 ± 2.29# | 47.67 ± 1.98# | 168.54 ± 4.31# |
| Chlorogenic acid of the present invention | 50 | 10 | 38.24 ± 2.75## | 4.12 ± 0.65## | 22.14 ± 2.41## | 162.25 ± 4.89## | 40.12 ± 3.15## | 139.21 ± 5.14## |
| Chlorogenic acid of the present invention | 70 | 10 | 38.75 ± 3.21## | 4.56 ± 0.78## | 22.87 ± 2.47## | 150.47 ± 5.23## | 38.48 ± 2.47## | 127.54 ± 6.54## |
| Chlorogenic acid of the present invention | 85 | 10 | 40.14 ± 6.12## | 4.32 ± 0.46## | 23.01 ± 1.58## | 145.21 ± 4.23## | 35.47 ± 2.46## | 119.25 ± 6.89## |
| Chlorogenic acid of the present invention | 100 | 10 | 41.56 ± 4.32## | 4.08 ± 0.85## | 23.48 ± 1.78## | 130.87 ± 2.89## | 33.14 ± 1.89## | 126.89 ± 4.21## |
| Chlorogenic acid of the present invention | 120 | 10 | 42.87 ± 3.15## | 3.89 ± 0.42## | 23.98 ± 2.14## | 127.21 ± 4.25## | 39.85 ± 2.41## | 138.84 ± 5.15## |
| Chlorogenic acid of the present invention | 140 | 10 | 44.78 ± 2.31## | 3.57 ± 0.64## | 24.35 ± 1.58## | 131.87 ± 2.65## | 40.08 ± 2.78## | 140.54 ± 6.12## |
| Chlorogenic acid of the present invention | 160 | 10 | 38.56 ± 2.45# | 4.05 ± 0.25# | 20.01 ± 1.47# | 194.45 ± 4.17# | 47.41 ± 2.54# | 157.98 ± 5.27# |
| Chlorogenic acid of the present invention | 180 | 10 | 37.25 ± 4.27# | 4.98 ± 0.87# | 19.87 ± 2.84# | 201.14 ± 6.14# | 48.17 ± 1.57# | 168.12 ± 4.89# |
| Chlorogenic acid of the present invention | 200 | 10 | 36.25 ± 2.87# | 5.45 ± 0.24# | 19.01 ± 1.58# | 209.41 ± 4.89# | 49.00 ± 1.25# | 177.56 ± 4.25# |
| Chlorogenic acid of the present invention | 220 | 10 | 30.12 ± 2.14 | 6.08 ± 0.45 | 17.24 ± 1.89 | 221.01 ± 2.75 | 51.24 ± 3.15 | 189.98 ± 5.67 |
| Commercially available chlorogenic acid | 10 | 10 | 26.15 ± 2.45 | 6.78 ± 0.32 | 12.57 ± 3.84 | 234.51 ± 3.15 | 58.67 ± 2.89 | 194.12 ± 6.32 |
| Commercially available chlorogenic acid | 20 | 10 | 27.24 ± 2.78 | 6.57 ± 0.47 | 13.62 ± 4.87 | 230.25 ± 4.13 | 57.41 ± 3.15 | 193.89 ± 3.84 |
| Commercially available chlorogenic acid | 35 | 10 | 28.05 ± 1.45 | 6.32 ± 0.87 | 14.83 ± 5.47 | 228.52 ± 5.03 | 56.84 ± 2.87 | 192.12 ± 5.12 |
| Commercially available chlorogenic acid | 50 | 10 | 29.14 ± 3.78 | 6.01 ± 0.65 | 15.57 ± 3.16 | 225.47 ± 3.84 | 56.88 ± 2.64 | 190.56 ± 4.28 |
| Commercially available chlorogenic acid | 70 | 10 | 30.55 ± 2.05 | 5.98 ± 0.48 | 16.88 ± 2.78 | 226.17 ± 2.45 | 55.14 ± 1.65 | 190.88 ± 3.65 |
| Commercially available chlorogenic acid | 85 | 10 | 31.04 ± 2.58 | 5.87 ± 0.41 | 17.37 ± 3.87 | 223.15 ± 3.61 | 53.24 ± 6.11 | 198.87 ± 2.78 |
| Commercially available chlorogenic acid | 100 | 10 | 32.54 ± 3.47 | 5.88 ± 0.46 | 18.00 ± 3.21 | 221.98 ± 3.15 | 51.54 ± 2.48 | 187.12 ± 4.57 |
| Commercially available chlorogenic acid | 120 | 10 | 33.65 ± 5.01 | 5.74 ± 0.85 | 18.24 ± 6.48 | 220.47 ± 3.84 | 50.18 ± 3.74 | 184.25 ± 3.49 |
| Commercially available chlorogenic acid | 140 | 10 | 33.29 ± 2.68 | 5.69 ± 0.42 | 18.65 ± 3.48 | 219.65 ± 5.14 | 48.87 ± 3.68 | 182.36 ± 3.87 |
| Commercially available chlorogenic acid | 160 | 10 | 33.12 ± 1.75 | 5.81 ± 0.54 | 17.55 ± 4.87 | 218.48 ± 3.84 | 49.28 ± 2.77 | 180.15 ± 6.48 |
| Commercially available chlorogenic acid | 180 | 10 | 32.87 ± 2.16 | 5.98 ± 1.02 | 17.98 ± 5.94 | 220.36 ± 4.65 | 50.00 ± 1.58 | 179.54 ± 4.16 |
| Commercially available chlorogenic acid | 200 | 10 | 31.11 ± 2.54 | 6.24 ± 0.85 | 16.49 ± 4.21 | 223.45 ± 3.47 | 51.21 ± 2.05 | 185.48 ± 3.94 |
| Commercially available chlorogenic acid | 220 | 10 | 28.15 ± 2.04 | 6.38 ± 0.48 | 15.31 ± 3.46 | 231.54 ± 5.08 | 50.13 ± 3.02 | 188.34 ± 5.87 |
| Model group | N.S | 10 | 27.35 ± 4.21 | 6.89 ± 0.32** | 12.87 ± 5.21 | 238.45 ± 5.12** | 58.57 ± 3.58** | 194.52 ± 6.12** |
| Negative group | N.S | 10 | 45.12 ± 2.56 | 3.48 ± 0.21 | 32.12 ± 2.48 | 104.98 ± 4.56 | 28.12 ± 3.25 | 97.68 ± 5.64 |

Note:
compared with the negative control group, **$P < 0.01$, *$P < 0.05$; compared with the model control group, ##$P < 0.01$, ##$P < 0.05$.

The invention claimed is:

1. A pharmaceutical preparation comprising a crystalline form of chlorogenic acid, wherein the crystalline form is of an orthorhombic system having a space group of P2$_1$2$_1$2$_1$, cell parameters of a=7.7291(2)Å, b=10.9808(2)Å, c=36.5334(7)Å, α=β=γ=90.00°, Z=8, and a cell volume of 3100.65(11)Å3, and wherein a clinical dosage of said preparation is 1.0-20 mg/kg per day.

2. The preparation according to claim 1, wherein the preparation is an oral preparation or an injection.

3. The preparation according to claim 2, wherein the clinical dosage of said injection is 1.0-6.0 mg/kg per day.

4. The preparation according to claim 2, wherein the clinical dosage of said oral preparation is 2-20 mg/kg per day.

5. The preparation according to claim 2, wherein the injection comprises 10-40 parts by weight of the crystalline form of chlorogenic acid, 1-5 parts by weight of antioxidant, and 60-100 parts by weight of scaffold.

6. The preparation according to claim 5, wherein every 1000 units of the injection comprises 30 grams of the crystalline form of chlorogenic acid, 2 grams of antioxidant, and 80 gram of scaffold.

7. The preparation according to claim 2, wherein the oral preparation comprises 80-150 parts of the crystalline form of chlorogenic acid, 700-900 parts by weight of a bulking agent, and 20-220 parts by weight of an adhesive agent, wherein the bulking agent is selected from starch, sugar, dextrin, lactose, amylum pregelatinisatum, microcrystalline cellulose, calcium sulfate, calcium hydrogen phosphate, mannitol, and mixtures thereof, and
  wherein the adhesive agent is selected from the group consisting of carboxymethylcellulose sodium, hydroxypropyl cellulose, methyl cellulose, ethyl cellulose, polyvinylpyrrolidone, and mixtures thereof.

8. The preparation according to claim 7, wherein 1000 units of the oral preparation comprises 100 grams of the crystalline form of the chlorogenic acid, and 100 gram of the adhesive agent.

9. A method of treating an immune system disease, comprising applying to a subject in need thereof the pharmaceutical preparation of claim 1 with one or more chosen from an antioxidant, a hepatoprotective and cholagogic drug, or an anti-virus drug, wherein the immune system disease is a small cell lung cancer, a liver cancer, a breast cancer, or a brain glioma.

10. The preparation according to claim 2, wherein the injection is a lyophilized powder injection.

11. The preparation according to claim 2, wherein the clinical dosage of said injection is 2-4 mg/kg per day.

12. The preparation according to claim 2, wherein the clinical dosage of said oral preparation is 5-14 mg/kg per day.

13. The preparation according to claim 5, wherein the antioxidant is sodium bisulfite and the scaffold is mannitol.

14. The preparation according to claim 5, wherein the injection comprises 30-40 parts by weight of the crystalline form of chlorogenic acid, 2-5 parts by weight of the antioxidant, and 80-90 parts by weight of the scaffold.

15. The preparation according to claim 7, wherein the oral prepa5ation comprises 80-100 parts of the crystalline form of chlorogenic acid, 800-900 parts by weight of the bulking agent, and 100-220 parts by weight of the adhesive agent.

* * * * *